United States Patent
Yamazaki et al.

(10) Patent No.: US 7,338,583 B2
(45) Date of Patent: Mar. 4, 2008

(54) ELECTROPHORESIS APPARATUS, AND METHOD OF ANALYSIS

(75) Inventors: Motohiro Yamazaki, Hitachinaka (JP); Kazumichi Imai, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 225 days.

(21) Appl. No.: 11/175,297

(22) Filed: Jul. 7, 2005

(65) Prior Publication Data

US 2006/0006066 A1    Jan. 12, 2006

(30) Foreign Application Priority Data

Jul. 12, 2004    (JP) ............................. 2004-204997

(51) Int. Cl.
*G01N 27/453*    (2006.01)
(52) U.S. Cl. ...................................... 204/601; 204/616
(58) Field of Classification Search ........ 204/450–470, 204/600–621
See application file for complete search history.

(56) References Cited

U.S. PATENT DOCUMENTS 6,652,724 B2 * 11/2003 Michael et al. ............. 204/613
7,005,053 B2 * 2/2006 Yamazaki et al. .......... 204/602
2002/0108857 A1 * 8/2002 Paschetto et al. ........... 204/457

FOREIGN PATENT DOCUMENTS

| EP | 1164200 A2 * | 12/2001 |
|----|--------------|---------|
| JP | 6-180302 | 6/1994 |
| JP | 8-271524 | 10/1996 |
| JP | 2003-166976 | 6/2003 |
| JP | 2003-185629 | 7/2003 |

OTHER PUBLICATIONS

Platestack product literature downloaded from the Perkin Elmer website on Apr. 16, 2007.*

* cited by examiner

*Primary Examiner*—Alex Noguerola
(74) *Attorney, Agent, or Firm*—Dickstein Shapiro LLP

(57) ABSTRACT

Analysis is performed efficiently in an electrophoresis apparatus while avoiding deterioration of samples. A plurality of sample plates are stored in frozen storage. When a particular sample plate is being analyzed, other sample plates are stored in a standby unit. In this way, a plurality of sample plates can be stored under cool conditions and analysis can be performed efficiently.

14 Claims, 10 Drawing Sheets

ELECTROPHORESIS APPARATUS, AND METHOD OF ANALYSIS

BACKGROUND OF THE INVENTION

1. Field of the Invention

The present invention relates to an electrophoresis apparatus for the separation analysis of nucleic acids, proteins, or the like. Particularly, it relates to a technique for storing sample plates in a capillary electrophoresis apparatus.

2. Background Art

Electrophoresis apparatuses have been proposed that can automatically perform continuous analysis for an extended period of time, using sample plates.

In such electrophoresis apparatuses capable of performing an automatic continuous analysis, many sample plates are stored.

Therefore, samples waiting for analysis are left standing at room temperature for a long time during a continuous operation. Leaving a sample at room temperature for a long time can cause deterioration of fluorescent dye or the hydrolysis of the dilution medium, such as formamide, resulting in a worsening of analysis performance.

During an automatic continuous analysis, a sample might be introduced for which an analysis result is immediately required, or some samples might turn out to require no analysis. In such cases, the order of arrangement of the already-stored sample plates must be changed.

Patent Document 1: JP Patent Publication (Kokai) No. 2003-344357 A (FIG. 3)

SUMMARY OF THE INVENTION

It is an object of the invention to prevent deterioration of samples and perform analysis efficiently in an electrophoresis apparatus.

In accordance with the invention, when a plurality of sample plates are stored in frozen storage, sample plates other than a particular sample plate being analyzed are stored in a standby unit. In this way, a plurality of sample plates can be stored under cooled conditions while performing analysis efficiently.

In accordance with the invention, efficiency and reliability of analysis can be improved.

These and other novel features and advantages of the invention will be more fully appreciated from the following detailed description when the same is read in connection with the accompanying drawings. It is to be understood, however, that the drawings are for the purpose of illustration only and are not intended as a definition of the limits of the invention.

DESCRIPTION OF THE PREFERRED EMBODIMENTS

Embodiment 1

Figure 1A:
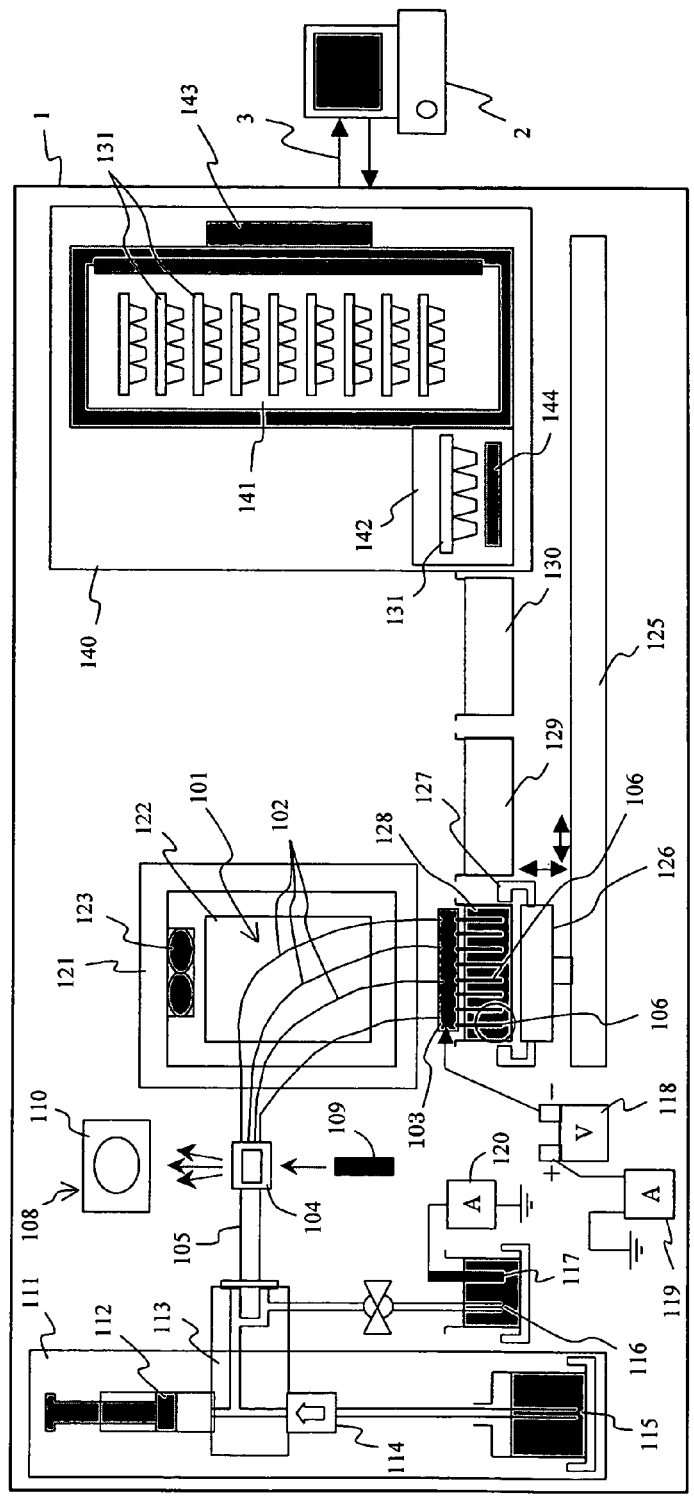
FIGS. 1A and 1B schematically show an electrophoresis apparatus.

FIG. 1 schematically shows an electrophoresis apparatus according to a first embodiment of the invention. As shown in FIG. 1A, the electrophoresis apparatus of this embodiment includes a capillary array 101 including one or more capillaries 102; a pump mechanism 111 for injecting a polymer into the capillaries; an optical detector unit 108 for optically detecting a sample in the capillaries; a high-voltage power supply 118 for applying high voltage to the capillaries; a first ammeter 119 for detecting the current produced by the high-voltage power supply; a second ammeter 120 for detecting a current that flows into an anode electrode; an oven 121 for maintaining the temperature of the capillaries at a constant level; a transport device 125 for transporting various containers to a capillary cathode end; and a sample plate storage unit 140.

The capillary array 101 includes 96 capillaries 102, a load header 103, a detector unit 104, a capillary head 105, and a capillary cathode end 106 at the opposite end of the capillary head. The capillary array 101 is a replaceable member. It is replaced when changing the method of measurement, or when a damage or deterioration of quality is found in the capillaries.

The capillaries 102 are each formed by a glass tube with an internal diameter of several tens to several hundreds of micrometers and an external diameter of several hundreds of micrometers. The surface of the capillaries 102 is coated with polyimide. The inside of the capillaries 102 is filled with a separation medium for providing an electrophoresis rate difference during electrophoresis. Separation media are available in both liquid and non-liquid forms; the present embodiment employs a liquid polymer.

Figure 1B:
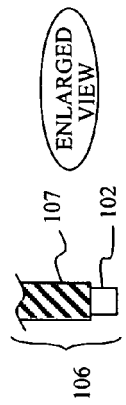

The capillaries 102 are bundled together with a capillary head 105. As shown in FIG. 1B, the capillary cathode end 106 is inserted into a metal hollow electrode 107, with the tip of the capillary protruding from the hollow electrode 107. The hollow electrode 107 is mounted on the load header 103.

The optical detector unit 108 includes a detecting portion 104, a light source 109, and an optical detector 110. At the detecting portion 104, the polyimide coating of the capillaries 102 is removed. When detecting a sample in the capillaries separated by electrophoresis, the detecting portion 104 of the capillaries is irradiated with a laser beam of light emitted by the light source 109. Light emitted from the detecting portion 104 is then detected by the optical detector 110, and, using the thus detected light, the sample is analyzed.

The pump mechanism 111 includes a syringe 112, a block 113, a check valve 114, a polymer bottle 115, and an anode buffer reservoir 116. Within the anode buffer reservoir 116, an electrode 117 is disposed.

The capillaries 102 can be loaded or reloaded with a polymer contained in the polymer bottle 115 by manipulating the syringe 112. The reloading of polymer in the capillaries is implemented for each measurement to achieve higher measurement performance.

The oven 121 is covered with a coating of heat-insulating material. It ensures a uniform and constant temperature of the capillary array 101 using a heating/cooling mechanism 122 and a fan 123.

The transport device 125 includes three electric motors and a linear actuator for moving a transport stage 126 in three axial directions, namely, vertical, horizontal, and depth directions. The transport stage 126 includes electric grippers 127 for carrying one or more containers. Thus, the transport stage 126 can transport a buffer reservoir 128, a water reservoir 129, a waste reservoir 130, and a sample plate 131 as necessary to the capillary cathode end.

The sample plate storage unit 140 includes a cooling bath 141 and a standby unit 142 for sample plates before measurement. The cooling bath 141 is fitted with a cooling mechanism 143, while the standby unit 142 for sample plates prior to measurement is fitted with a heating mechanism 144. As shown in the drawing, a plurality of sample plates 131 are stored in the cooling bath 141, and they are moved to the standby unit 142 by the transport device 125 immediately prior to analysis. In the standby unit 142, each sample plate 131 is heated by the heating mechanism 144.

An apparatus main body 1 is connected to a control computer 2 via a communications cable 3. An operator can control the functions of the apparatus via the control computer 2 and receive data detected by the detector in the apparatus.

When an analysis is conducted using the electrophoresis apparatus, a pre-run is initially performed, as will be described with reference to FIG. 5 later. A pre-run is conducted so that the state of the polymer in the capillaries can be rendered suitable for analysis prior to the main analysis step involving electrophoresis. In a pre-run, generally a voltage on the order of several to several tens of volts is applied between the anode electrode 117 and the cathode electrode 107 for a period of several to several tens of minutes.

During electrophoresis, a high voltage produced by the high-voltage power supply 118 is applied between the anode electrode 117 and the cathode electrode 107 in order to give the samples in the capillaries a mobility by the action of the electric field produced between the cathode and anode buffers. The samples are then separated by the difference in mobility, which depends on the property of the samples. The thus separated samples are detected optically in the order of arrival at the detecting portion 104. For instance, when the samples are DNA, differences in mobility arise due to their different base lengths. DNA with shorter base lengths has higher transfer rates, and therefore they pass the detecting portion earlier. Normally, the measurement time and the period of application of voltage are determined in accordance with the sample with the longest electrophoresis time.

Figure 2:
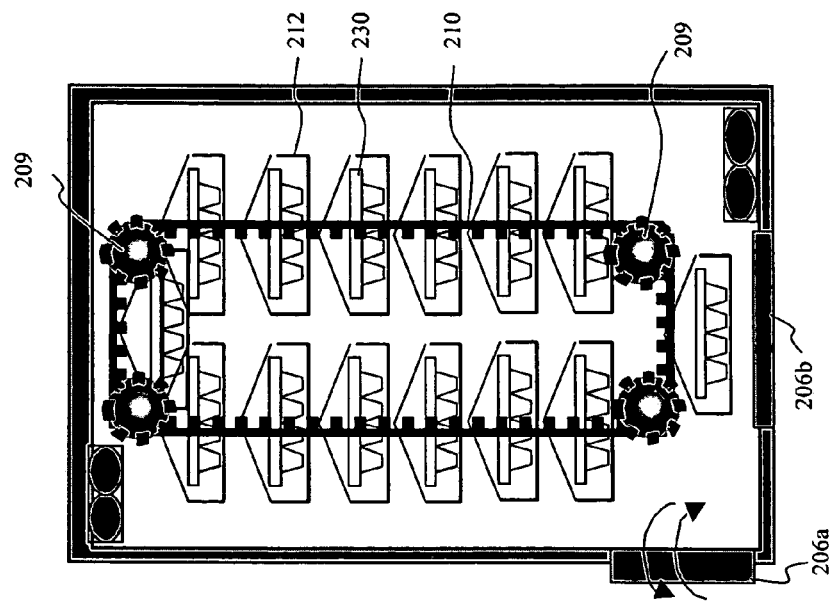
FIGS. 2A and 2B schematically show a sample plate storage unit in a first example of the electrophoresis apparatus.
Figure 2:
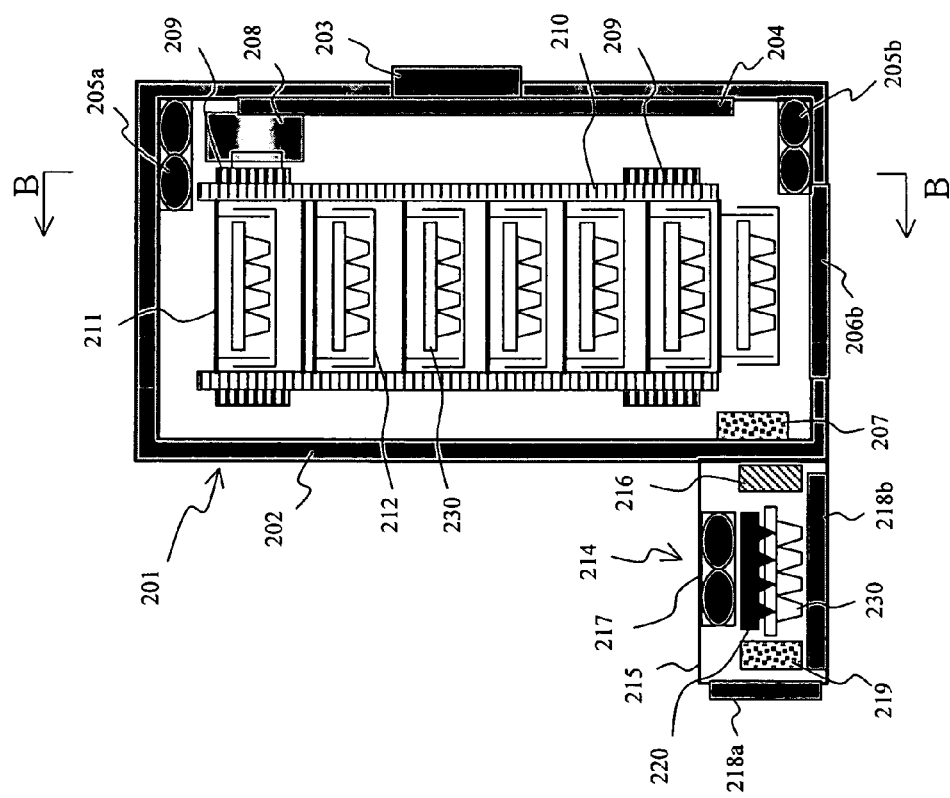

With reference to FIG. 2, an example of the sample plate storage unit of the present embodiment is described. The sample plate storage unit includes a cooling bath 201 and a standby unit 214 for storing sample plates before measurement. The cooling bath 201 includes: a casing 202 constructed of heat-insulating material; an electric cooling source 203 consisting of a peltiert device or the like; a heat-conducting plate 204 with high heat conductivity connected to the cooling source 203; fans 205a and 205b for air circulation disposed at the top and bottom of the apparatus; two sample plate entrances 206a and 206b; and a sample detector 207. The cooling bath 201 contains a motor 208; four rotatable gears 209; a belt or chain 210 engaged with the gears; support axles 211 attached to the belt 210 at regular intervals; and racks 212 rotatably mounted on the support axles for mounting sample plates. Of the two sample plate entrances 206a and 206b, the entrance 206a provided at the side is used when the operator carries sample plates 230 in or out. The other entrance 206b provided at the bottom is used when the operator carries sample plates 230 using the transport device 125.

The racks 212 are suspended by the support axles 211 in the Ferris wheel fashion, and they rotate by their own weights. Thus, the sample plates 230 laid on the racks 212 can be horizontally retained at all times.

The standby unit 214 includes a casing 215 constructed of heat-insulating material; a heating mechanism 216; an air-circulating fan 217; two sample plate entrances 218a and 218b; a sample detector 219; and a film removing mechanism 220. Of the two sample plate entrances 218a and 218b, the entrance 218a provided at the side is used when the operator carries the sample plates 230 in or out. The entrance 218b provided at the bottom is used when the operator carries the sample plates 230 in or out using the transport device 125.

The sample plates 230 are each provided with a number of wells for storing samples. After the wells are loaded with samples, normally a transparent film is affixed thereon so as to prevent the evaporation of the samples or their contamination with dust, for example.

In the present embodiment, the racks 212 in the cooling bath 201 are loaded with the sample plates 230 with the film affixed thereto. Further, in the present embodiment, the sample plates 230 are given an identification code for identifying the individual sample plates. The identification code is read by the sample detectors 207 and 219, which then transmit the code to control computer 2. Using the identification code, the control computer 2 manages the sample plates 230. The identification code may be a bar code, and the sample detectors 207 and 219 may be bar-code readers. The control computer 2 analyzes and displays the information contained in the identification code.

The sample plates 230 may be commercially available microtiter plates, which are sold by various companies with a variety of shapes. Microtiter plates, which contain wells for storing samples, come in two types, one with 96 (8×12=96) wells and the other with 384 (16×24=384) wells.

A 384-well sample plate measures approximately 1 cm in height, 13 cm in length, and 8 cm in width. A 96-well sample plate measures approximately 2 cm in height, 13 cm in length, and 8 cm in width. The size of the cooling bath is 10 cm in width, 30 cm in length, and 1.5 m in height. When the racks 212 for carrying the sample plates are installed at 3 cm intervals, approximately 100 sample plates 230 can be stored.

The inside of the cooling bath 201 is cooled by the cooling source 203 so that a sample solution carried on the sample plates 230 can be frozen. The racks 212 on which the sample plates 230 for analysis are laid are initially disposed at the bottom of the cooling bath 201.

Then, the transport stage 126 is brought below the cooling bath 201 by the transport device 125. The entrance 206b at the bottom of the cooling bath 201 is then opened, and the transport stage 126 is moved upwards by the transport device 125. The transport stage 126 is thereafter inserted into the cooling bath 201 via the entrance 206b, which is now open. The grippers 127 fitted to the transport stage 126 then grip the sample plate laid on the lowermost rack.

The transport stage 126 is then moved downwards by the transport device 125 and is moved further below the standby unit 214. The entrance 206b of the cooling bath 201 is closed, and instead the entrance 218b at the bottom of the standby unit 214 is opened. The transport stage 126 is moved upwards by the transport device 125 and is inserted into the standby unit 214 via the entrance 218b, which is now open. The grippers 127 are then opened, whereby the sample plate is disposed within the standby unit 214. The transport stage 126 is moved downwards by the transport device 125, and then the entrance 218b is closed.

Inside the standby unit 214, the frozen sample solution is thawed using the heating mechanism 216. If a dew forms on the surface of the sample plate 230, it is removed by the circulation of air produced by the air-circulating fan 217.

The sample solution may be heated by the heating mechanism 216 up to approximately 80° C., for example, so that the DNA in the sample solution can be heat-denatured, namely, the double helix can be rendered into single strands. In this way, the heating mechanism 216 can provide not only a thawing function but also an analysis processing function.

The film that protects the sample on the sample plates 230 in the sample plate standby unit 214 is removed by the film removing mechanism 220. The film removing mechanism 220 includes a needle, for example, for forming an opening in the film. The sample plates 230 are carried out of the standby unit 214 via the entrance 218b by the transport device 125 and then transported to the capillary cathode end. The electrode portion of the capillaries is inserted into the opening made in the film on each sample plate 230, thus making preparations for the loading of the capillaries 102 with samples.

Figure 3:
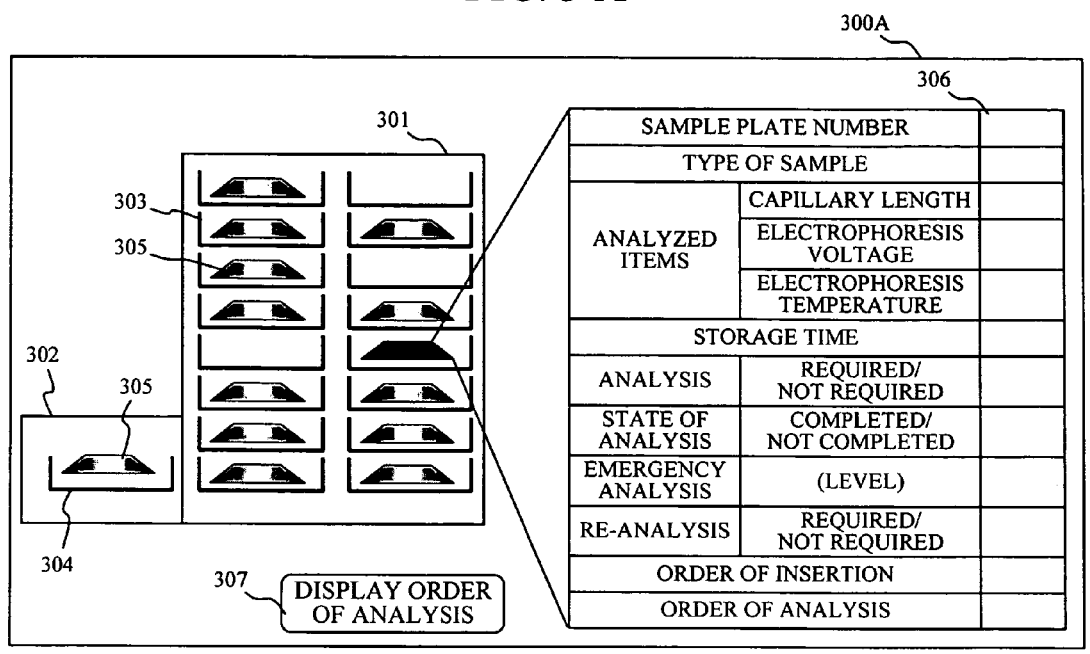
FIGS. 3A and 3B show examples of a screen displaying information about sample plates.
Figure 3:
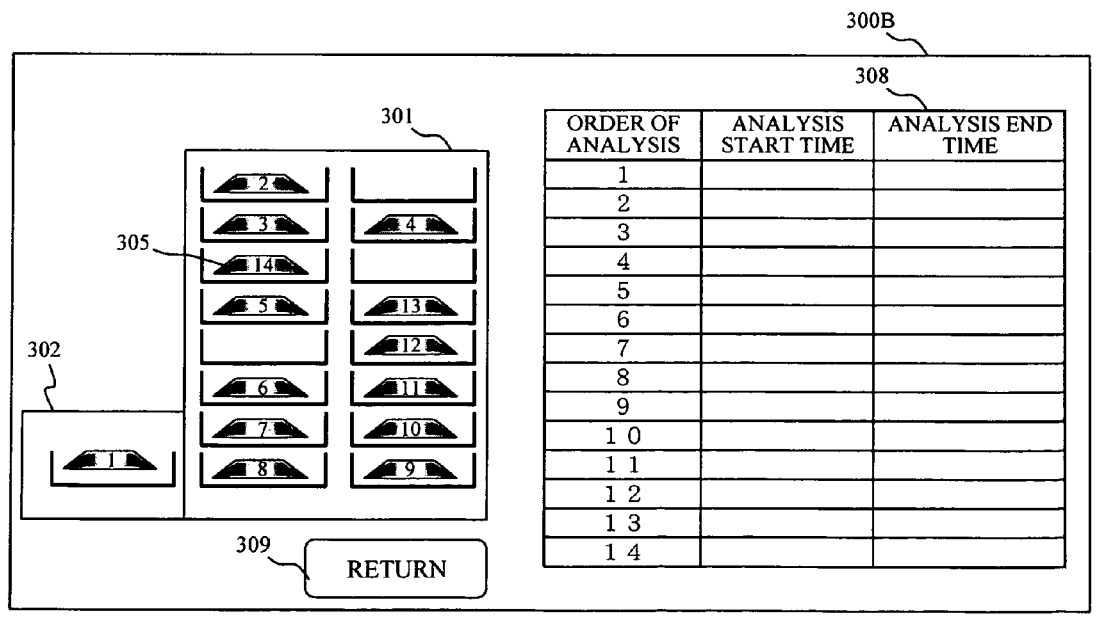

With reference to FIG. 3, a method of displaying the information about the sample plates is described. FIG. 3 shows an example of the screen displayed on a display unit installed on the control computer 2. As shown in FIG. 3A, a screen 300A depicts a cooling bath model 301 schematically representing the cooling bath; a standby unit model 302 schematically representing the sample plate standby unit; rack models 303 and 304 schematically representing the racks; and a sample plate model 305 schematically representing the sample plates. These models represent the actual cooling bath and the sample plate standby unit. Therefore, the number of the rack models 303 and 304 is equal to the number of the actual racks. Similarly, the number of the sample plate models 305 on the rack models is equal to the number of actual sample plates. If no sample plate model is depicted on the rack models, this indicates that the actual racks are also empty.

When a particular sample plate 305 is clicked, information 306 about that sample plate is displayed. The information 306 contains: sample plate number; type of sample; analyzed content (capillary length, electrophoresis supply voltage, and electrophoresis temperature); storage time; analysis (required/not required); state of analysis (finished/not finished); urgency of analysis (in levels); re-analysis (required/not required); order of insertion; and order of analysis, for example.

When a "Display analysis order" button 307 on the screen 300A is clicked, a screen 300B shown in FIG. 3B is displayed. On the screen 300B, the number indicating the order of analysis is displayed in the sample plate model 305.

Also on the screen 300B, a schedule chart 308 showing the order of analysis is displayed. The schedule chart 308 includes analysis order, analysis start time, and analysis end time. Normally, the time required for electrophoresis is determined by the kind of analysis. Thus, when the analysis order is given, the start time and end time of analysis of all of the sample plates can be determined. The manner of determining the analysis order will be described later. When a "Return" button 309 on the screen 300B is clicked, the screen 300A shown in FIG. 3A is displayed.

In the present embodiment, the operator, once a continuous analysis is started, can be informed of when the analysis of which sample plate is started and completed, thereby eliminating the need to monitor the apparatus at all times. The operator can control multiple devices by simply monitoring them at required times. Further, the individual screens are switchable, so that the operator can gain necessary information at any time.

The screen shown in FIG. 3 is displayed on a small-sized display unit mounted on the cooling bath, as well as on the display unit installed on the control computer 2. Such a small-sized display unit may be installed at the sample plate entrance 206a of the cooling bath, for example.

Figure 4:
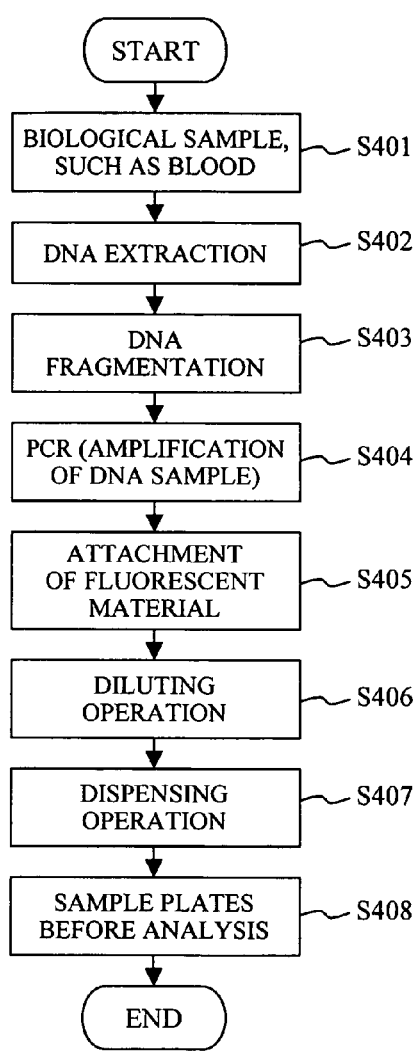
FIG. 4 shows a procedure for preparing a sample plate to be analyzed.

With reference now to FIG. 4, a method of manufacturing an analysis sample plate is described. In step S401, a biological sample, such as blood, as an analyzed object is prepared. In step S402, DNA is extracted from the chromosome of a cell. In step S403, the extracted DNA is cut by an enzyme into small pieces to prepare specimens of the analyzed object. In step S404, the prepared sample is amplified by polymerase chain reaction (PCR). In step S405, a fluorescent labeling substance is attached to the sample. In step S406, the prepared DNA sample is diluted with pure water or formamide, for example. In step S407, a microtiter plate is selected for the particular purpose, and then a dispensing operation is carried out to load each well with the sample. In step S408, a sample plate to be inserted into the electrophoresis apparatus is prepared. Then, a film is affixed to the sample plate.

Now referring to FIG. 1, preparations to be made prior to the start of electrophoresis are described. Prior to measurement, the operator prepares the following: the polymer bottle 115 with a polymer as a separating medium in it; the anode buffer reservoir 116 containing a buffer solution; a cathode buffer reservoir 128 containing the buffer solution; a water reservoir 129 containing pure water for washing the capillaries; a waste reservoir 130 into which the polymer in the capillaries is to be discharged; and a sample plate 131 carrying the sample to be measured. The anode buffer reservoir 116 is filled with the buffer to such an extent that both the electrode (GND) 117 and the communicating tube are sufficiently submerged. The cathode buffer reservoir 128 is filled with the buffer to such an extent that the hollow electrode 107 and the capillary cathode end 106 are sufficiently submerged.

If the measurement is started when the level of buffer is not high enough, or when the buffer reservoirs are empty, there is the danger that a discharge might occur between the high-potential cathode electrode and other parts of lower potential upon application of high voltage. Further, it is desirable that the buffer levels in the anode buffer reservoir 116 and the cathode buffer reservoir 128 are the same. This is to ensure that the polymer in the capillaries is not shifted by the pressure produced by the difference in the buffer levels. It is also necessary that the passages utilized for electrophoresis, or the passages used for carrying polymer to these passages, all be filled with the polymer prior to measurement. Normally, when the electrophoresis apparatus is continuously operated, these passages are filled with polymer. When the passages are to be refilled with polymer for replacement of the capillary array or after the washing of the passages, the pump mechanism of the apparatus is operated, or the syringe is operated by the operator manually. After loading or reloading of polymer, the operator visually inspects to make sure that there is no bubbles or foreign matter in the passages. Finally, the operator enters predetermined settings in the control computer, and then begins measurement.

Figure 5:
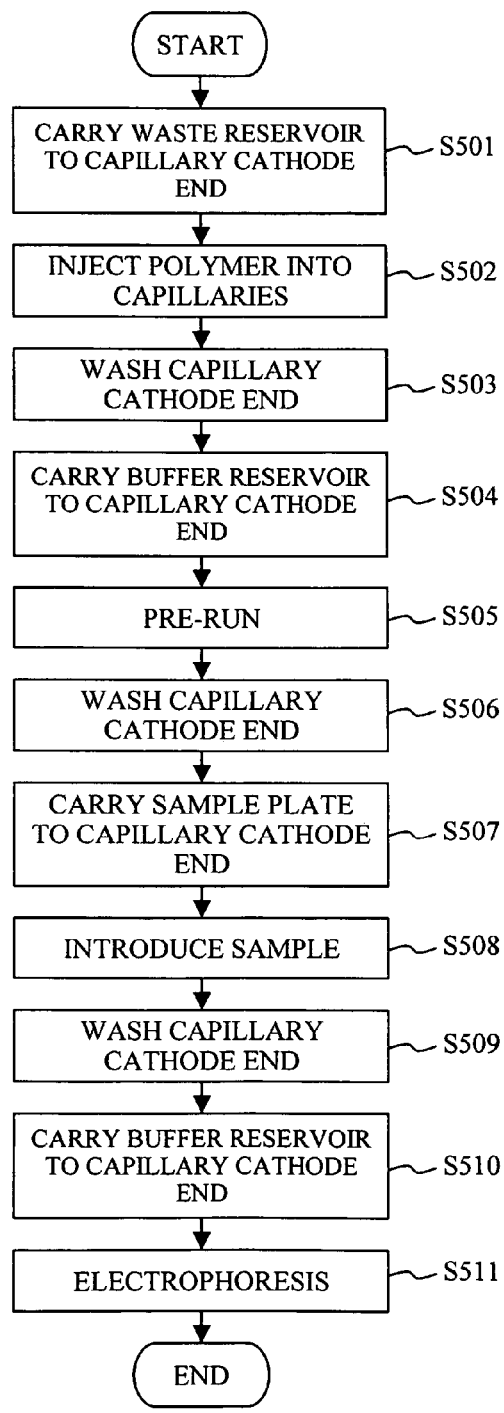
FIG. 5 shows an analysis procedure, from start to end thereof.

With reference to FIG. 5, the procedure for analysis from start to finish thereof is described. Reference will also be made to FIG. 1. The electrophoresis apparatus starts an analysis in response to an instruction from the control computer 2. In step S501, the waste reservoir 130 is transported by the transport device 125 to the capillary cathode end 106. In step S502, polymer is injected by the pump mechanism 111 into the capillaries. In step S503, the waste reservoir 130 is transported to the original position and the water reservoir 129 is transported to the capillary cathode end 106, using the transport device 125. The capillary cathode end 106 is immersed in the pure water in the water reservoir 129 to perform washing. In step S504, the water reservoir 129 is returned to the original position, and the buffer reservoir 128 is transported to the capillary cathode end 106, using the transport device 125. In step S505, a pre-run is carried out. As mentioned above, during the pre-run, a voltage on the order of several to several tens of kilovolts is applied between the anode electrode 117 and the cathode electrode 107 for several to several tens of minutes.

In step S506, the buffer reservoir 128 is returned to the original position, and the water reservoir 129 is transported to the capillary cathode end 106, using the transport device 125. The capillary cathode end 106 is washed with the pure water in the water reservoir 129. In step S507, the water reservoir 129 is returned to the original position and the sample plate 131 is transported to the capillary cathode end 106, using the transport device 125. In step S508, the sample in the sample solution is introduced into the capillaries. The capillary cathode electrode 107 is immersed in the sample solution, and a voltage on the order of several kilovolts is applied, whereby an electric field is produced between the sample solution and the anode electrode 117. The electric field causes the sample in the sample solution to be introduced into the capillaries.

In step S509, the sample plate 131 is returned to the original position and the water reservoir 129 is transported to the capillary cathode end 106, using the transport device 125. The capillary cathode end 106 is washed. In step S510, the water reservoir 129 is returned to the original position and the buffer reservoir 128 is transported to the capillary cathode end 106, using the transport device 125. In step S511, electrophoresis is carried out, in which, as mentioned above, a high voltage from the high-voltage power supply 118 is applied between the anode electrode 117 and the cathode electrode 107. After a predetermined time has elapsed from the start of application of voltage and planned data has been collected, the application of voltage is terminated to end electrophoresis, thereby completing the measurement sequence.

Figure 6:
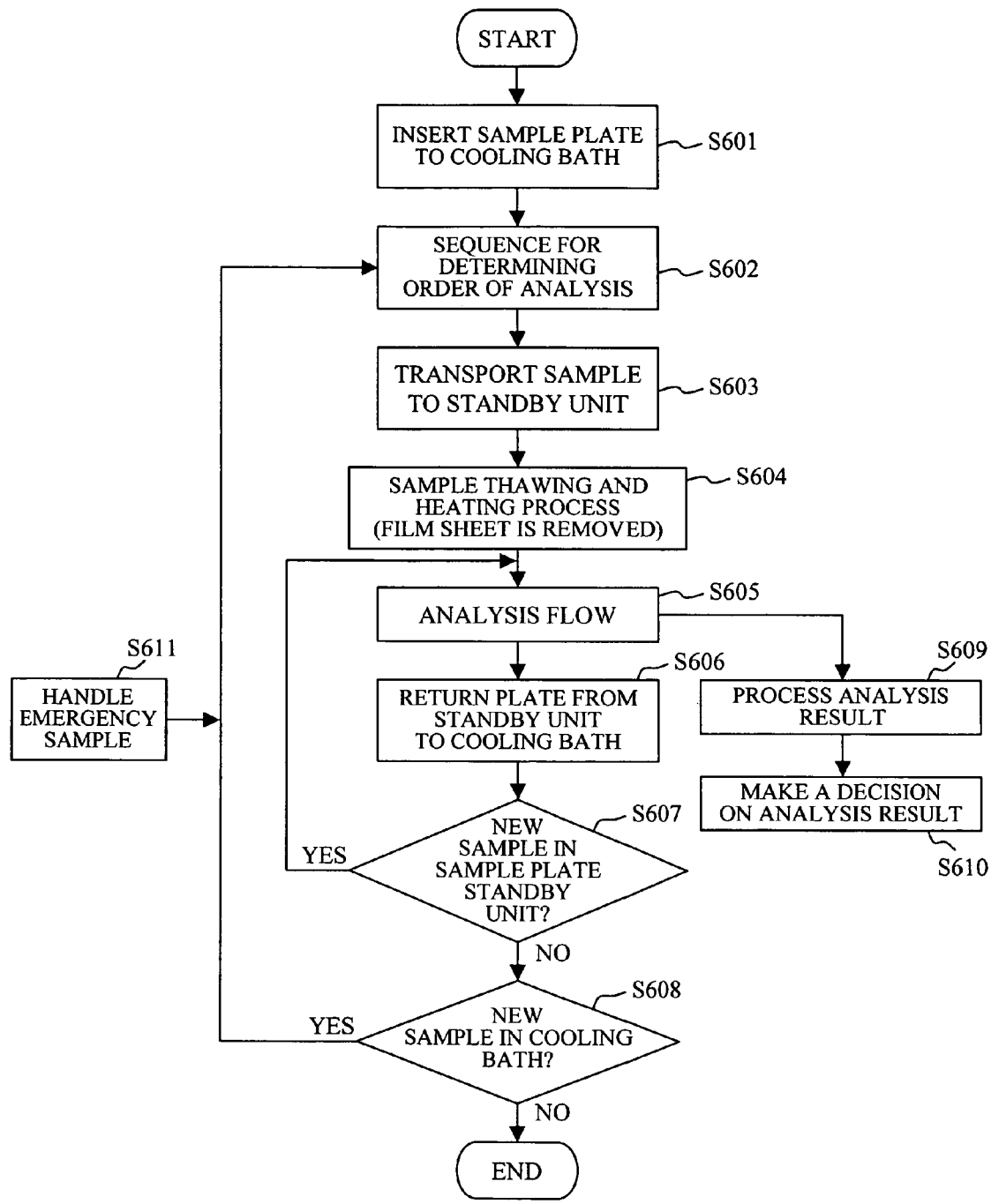
FIG. 6 shows an automatic continuous analysis flow involving an electrophoresis apparatus.

Next, with reference to FIG. 6, the procedure for continuously analyzing a number of sample plates using the electrophoresis apparatus of the present embodiment is described. Reference will also be made to FIG. 2. In this example, the analysis process for a number of sample plates can be carried out continuously, automatically, and efficiently based on the information about the sample plates.

In step S601, the operator inserts a plurality of sample plates 230, which are the analyzed objects, into the cooling bath 201. The operator then disposes the sample plates 230 on the rack 212 via the entrance 206a of the cooling bath. The operator then determines the type of each sample plate 230 and the type of analysis, and incorporates them in the analysis flow, using the control computer 2. In step S602, the control computer 2 determines the analysis order by referring to the information about the sample plates 230. Examples of the sequence for determining the analysis order will be later described with reference to FIGS. 7, 8, and 10. In step S603, the sample plates 230 are carried by the transport device 125 from the cooling bath 201 to the standby unit 214, in the order of analysis determined. In step S604, the sample is thawed and heated. The film affixed to the sample plates is removed by the film removing mechanism 220. In step S605, the sample plates 230 disposed in the standby unit 142 are transported by the transport device 125 to the capillary cathode end, where an analysis process is carried out, as has already been described with reference to FIG. 5. After the analysis process is completed, the sample plates 230 are transported by the transport device 125 from the capillary cathode end to the standby unit 142.

In step S606, the sample plates 230 that have been analyzed are returned by the transport device 125 from the standby unit 214 to the cooling bath 201. In step S607, it is determined whether or not there is any sample plate 230 in the standby unit 214 that has not yet been analyzed. If there is such a sample plate 230, the routine returns to step S604, where an analysis process is performed. If not, the routine proceeds to step S608.

In step S608, it is determined whether or not there is any sample plate 230 in the cooling bath 201 for which the order of analysis has not yet been determined. If there is a sample plate 230 for which the order of analysis is not determined, the routine returns to step S602, where the order of analysis is determined. If there is no such sample plate, the routine ends.

In step S609, the analysis result for the sample plate 230 for which analysis has been completed is automatically processed. In step S610, based on the processed analysis result, an instruction for re-analysis is issued for a necessary sample, and an instruction is also issued to stop the analysis of a sample or samples that have been prepared under identical conditions. An example of the processing performed in step S610 will be described later with reference to FIG. 9.

In step S611, an emergency or interrupt sample process is performed. In the present example, the emergency or interrupt sample can be inserted at any time at the discretion of the operator. When the emergency or interrupt sample is to be inserted, the routine returns to step S602 to determine the order of analysis once again. The details of the emergency or interrupt analysis process will be described later with reference to FIG. 8.

Figure 7:
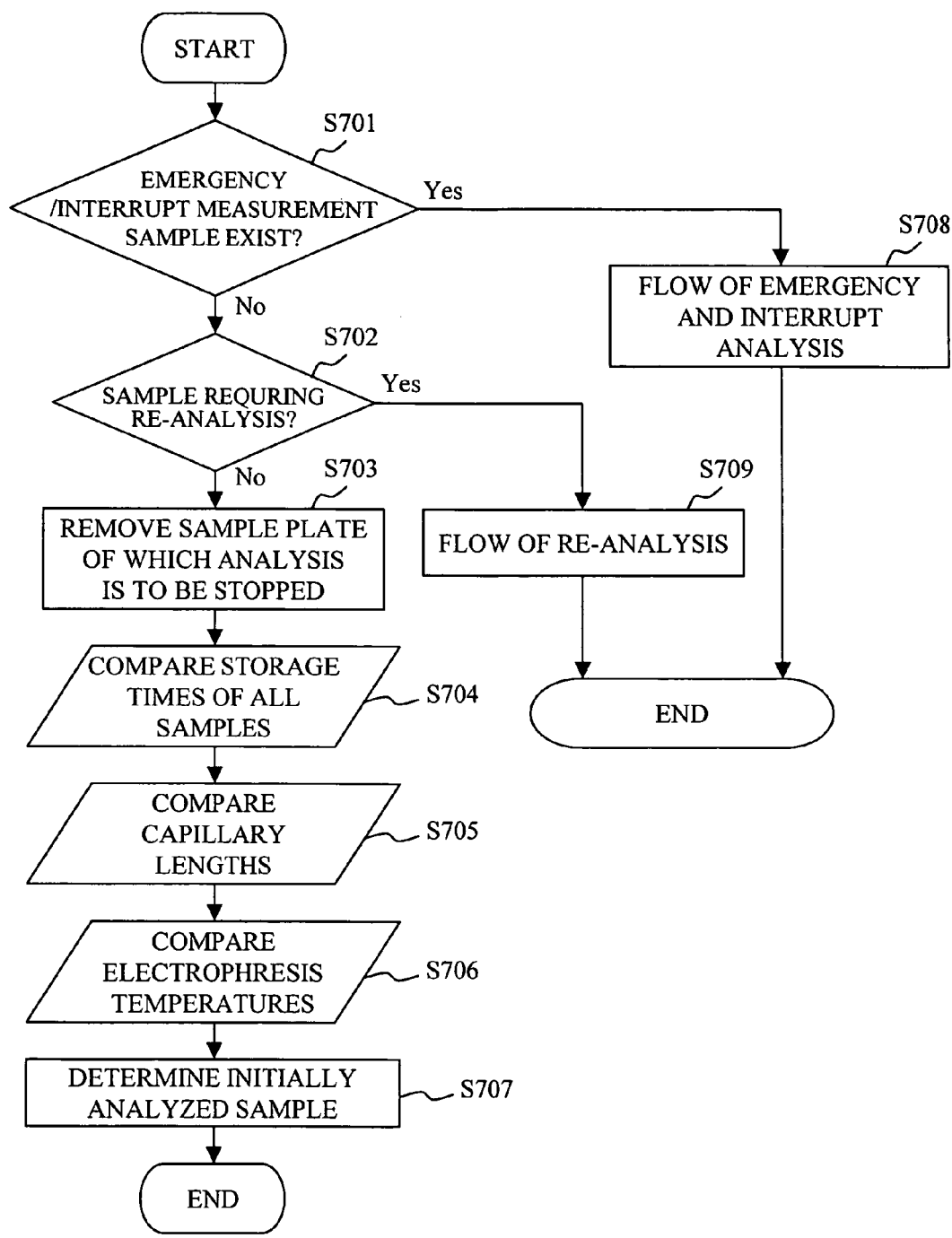
FIG. 7 shows a process for determining the order of analysis.

With reference to FIG. 7, a method of determining the order of analysis of a plurality of sample plates 230 is described. In step S701, it is determined if there is a sample plate among the sample plates stored in the cooling bath 141 that requires an emergency or interrupt sample analysis. If there is a sample plate for which an emergency or interrupt analysis is required, the routine goes to step S708. The details of step S708 will be described with reference to FIG. 8. In step S702, it is then determined if there is a sample plate among the sample plates stored in the cooling bath 141 for which re-analysis is required. If there is a sample plate that requires re-analysis, the routine proceeds to step S709, the details of which will be described later with reference to FIG. 10.

In step S703, it is determined if there is a sample plate among the sample plates stored in the cooling bath 141 for which analysis must be terminated. If there is a sample plate for which analysis must be stopped, an instruction is issued to stop its analysis.

In step S704, the storage times of all of the samples are compared. The sample storage time is recorded when the sample plates are stored in the cooling bath 141.

In step S705, the capillary lengths of all of the samples are compared. The capillary lengths of the samples are recorded when the sample plates are stored in the cooling bath 141.

In step S706, the electrophoresis temperatures of all of the samples are compared. The electrophoresis temperatures for the samples are recorded when the sample plates are stored in the cooling bath 141.

In step S707, the initial sample plate to be analyzed is determined based on the storage time, capillary length, and electrophoresis temperature determined in steps S704 to S706.

An example of determining the initially analyzed sample plate based on the storage time will be described. If the samples are stored for a long time, they could undergo alterations or deteriorate. Therefore, samples that have been stored for longer times are preferentially analyzed in order to avoid alteration or deterioration.

The following is another example where the initially analyzed sample plate is determined based on the capillary length. For those samples with identical capillary lengths, there is no need to replace the capillary array, and therefore analysis is preferably carried out continuously. Those samples with shorter capillary lengths have shorter analysis time than those samples with longer capillary lengths. Therefore, samples with shorter capillary lengths are preferably analyzed before samples with longer capillary lengths. For instance, when there is a sample with the capillary length of 36 cm and another sample with the capillary length of 50 cm, the sample with the capillary length of 36 cm is preferably preferentially processed.

Finally, an example where the initially analyzed sample plate is determined based on the electrophoresis temperature will be described. The oven for controlling the electrophoresis temperature requires several tens of minutes before a target electrophoresis temperature is reached. Thus, the samples with the same electrophoresis temperature are preferably analyzed in a continuous manner. In the oven, it takes less time to switch from higher temperatures to lower temperatures than from lower to higher temperatures. Therefore, samples with higher electrophoresis temperature are preferably analyzed before the samples with lower electrophoresis temperatures. For example, when there is a sample with the electrophoresis temperature of 60° C. and another sample with the electrophoresis temperature of 50° C., the oven 121 is initially set for 60° C. and the sample with the electrophoresis temperature of 60° C. is analyzed, and once its analysis is completed, then the oven 121 is set for 50° C. and the sample with the electrophoresis temperature of 50° C. is analyzed.

In the present example, the conditions for determining the initially analyzed sample plate consisted of the storage time, capillary length, and electrophoresis temperature. Other conditions might include electrophoresis voltage, for example. These conditions are merely exemplary and may be designated by the operator as desired.

Figure 8:
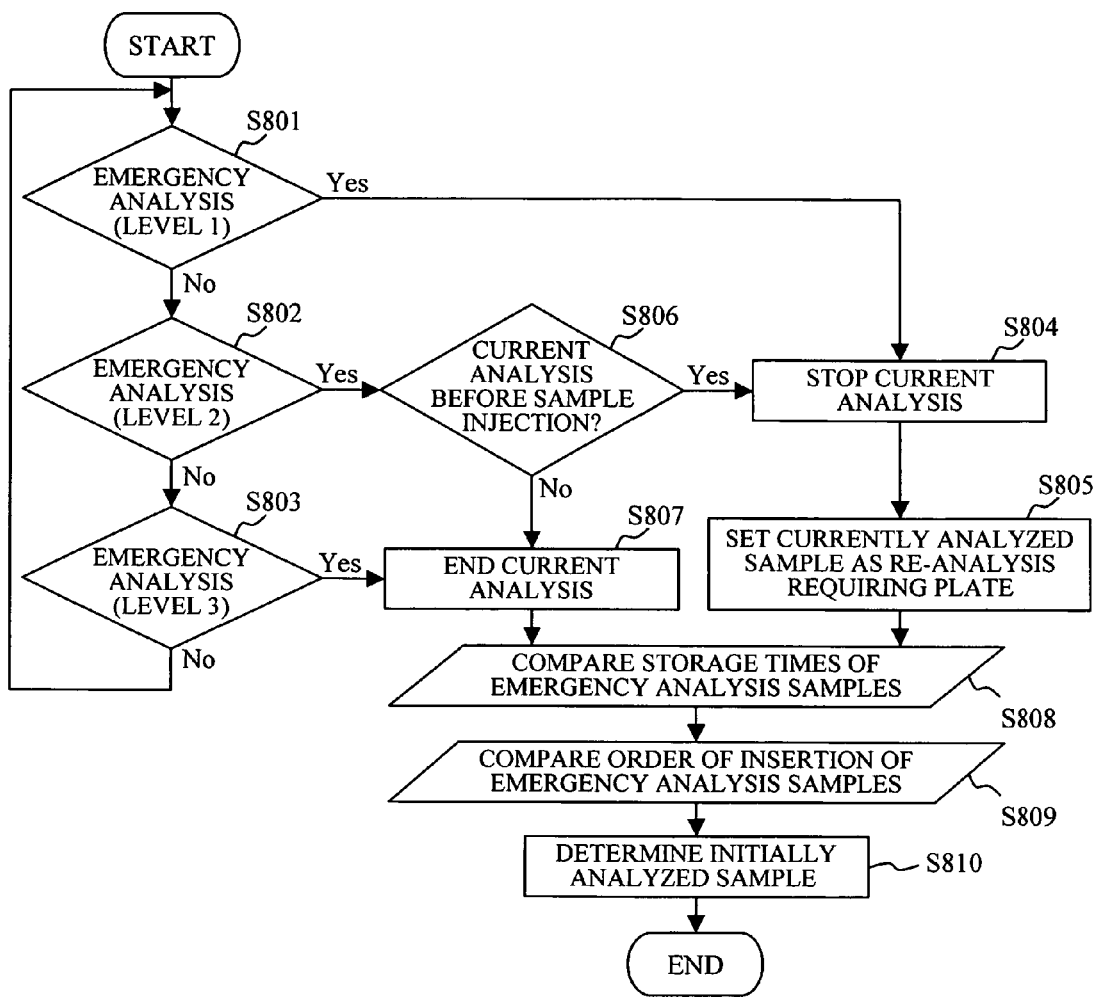
FIG. 8 shows a process for determining the analysis order for an emergency or interrupt analysis.

With reference now to FIG. 8, the flow of the emergency or interrupt analysis in step S708 of FIG. 7 is described. The operator allocates three levels of emergency to the sample plates for emergency or interrupt analysis, namely, levels 1, 2, and 3 in decreasing order of emergency. The emergency levels for the sample plates are recorded in the control computer 2. After the emergency levels have been entered, the sample plate for emergency or interrupt analysis is put in the cooling bath 141. Alternatively, the sample plate may be put in the standby unit 142.

In step S801, it is determined whether or not the particular sample plate for emergency or interrupt analysis has emergency level 1. If its emergency level is 1, the currently conducted electrophoresis analysis is terminated in step S804. Then, in step S805, the sample plate for which the analysis has been interrupted is issued an instruction for re-analysis, and the sample plate is then returned to the cooling bath 141.

If the emergency level is not 1, the routine proceeds to step S802, where it is determined if the emergency or interrupt analysis sample plate has emergency level 2. If the emergency level is 2, it is determined in step S806 whether the currently conducted electrophoresis analysis is at a stage prior to the injection of sample. If it is before the injection of sample, this indicates that the analysis is now at the stage of polymer injection or pre-run, and electrophoresis has yet to be performed. Therefore, the routine proceeds to step S804, where the currently conducted electrophoresis analysis is stopped. If it is after the injection of sample into the capillaries, the routine proceeds to step S807 where the currently conducted electrophoresis analysis is completed.

If the emergency level is not 2, the routine proceeds to step S803, where it is determined whether the emergency or interrupt analysis sample has emergency level 3. If the emergency level is 3, the routine proceeds to step S807, where the currently conducted electrophoresis analysis is completed. If it is not emergency level 3, the routine returns to step S801.

In step S808, when there are a plurality of sample plates for emergency or interrupt analysis, their storage times are compared. In step S809, when there are a plurality of sample plates for emergency or interrupt analysis, the order in which they were put in the cooling bath 141 is compared. In step S810, the initially analyzed sample is determined. The initially analyzed sample may be determined on the basis of the storage time or the order of insertion into the cooling bath.

Figure 9:
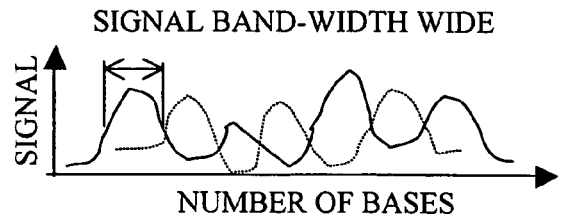
FIGS. 9A and 9B are drawings for the explanation of a process for making a decision on an analysis result.
Figure 9:
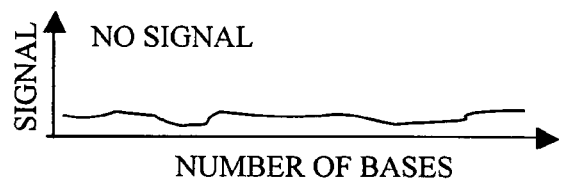

With reference to FIG. 9, the process in step S610 of making a decision on the result of analysis is described. A fluorescent detected signal obtained by electrophoresis indicates the base sequence of DNA. Normally, the fluorescent detected signal is shown in a peak that depends on the number of bases that have been separated. The smaller the number of bases, the narrower the half-width of the peak signal becomes; conversely, the larger the number of bases, the wider the half-width becomes. However, due to failures in the pre-processing of the sample, or deterioration in the separating medium, the signal width could become wider, as shown in FIG. 9A. As a result, the resolution of base sequences could become lower than the capability of the apparatus. Therefore, if the half-width of the signal in the analysis result is greater than the nominal performance of the apparatus relative to the number of bases, the sample is judged to require re-analysis, and an instruction is issued to the apparatus screen operator, as shown in FIG. 3, to replace the separating medium or the buffer solution.

If the fluorescent detected signal is not obtained, as shown in FIG. 9B, it is judged that there is something wrong with the sample itself. In such a case, analysis of the samples prepared under identical conditions (such as the PCR process, diluting medium, and the addition of fluorescent substance) is terminated.

Figure 10:
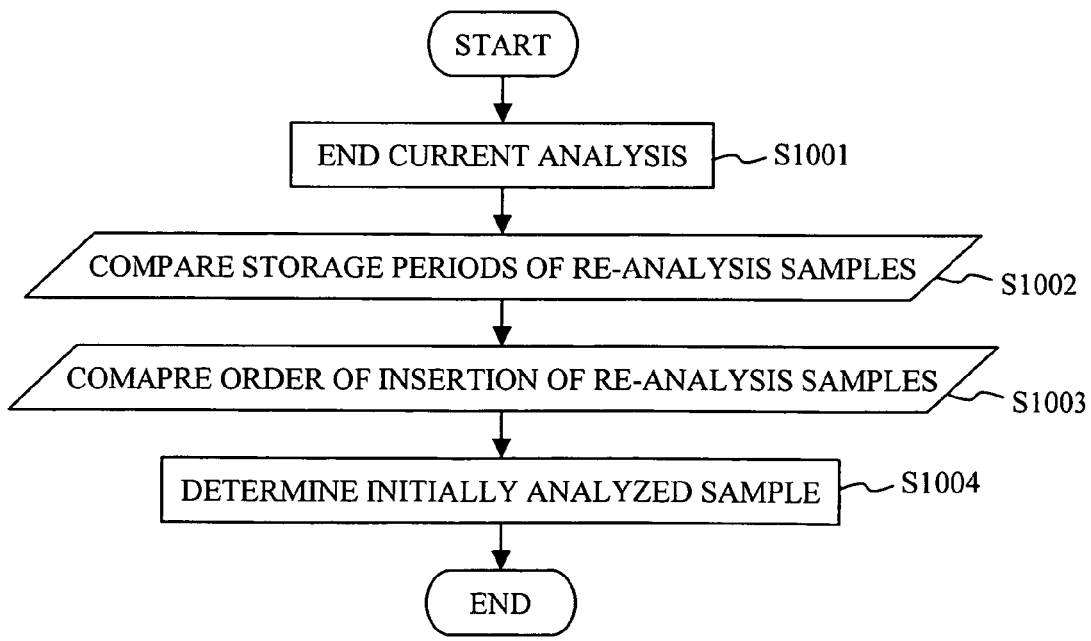
FIG. 10 shows a process for determining the analysis order for re-analysis.

With reference to FIG. 10, the flow of determining the order of re-analysis in step S709 in FIG. 7 is described. In step S1001, the currently conducted electrophoresis of a sample plate is completed. In step S1002, the storage times of all of the sample plates requiring re-analysis are compared. In step S1003, the capillary lengths of all of the sample plates requiring re-analysis are compared.

In step S1004, the initially analyzed sample is determined. If the analysis order is determined on the basis of the storage time of the samples, samples with longer storage time are preferentially analyzed. If the analysis order is determined on the basis of the capillary length, samples with shorter capillary lengths are preferentially analyzed before samples with longer capillary lengths. Samples with identical capillary lengths are continuously analyzed.

Embodiment 2

Figure 11:
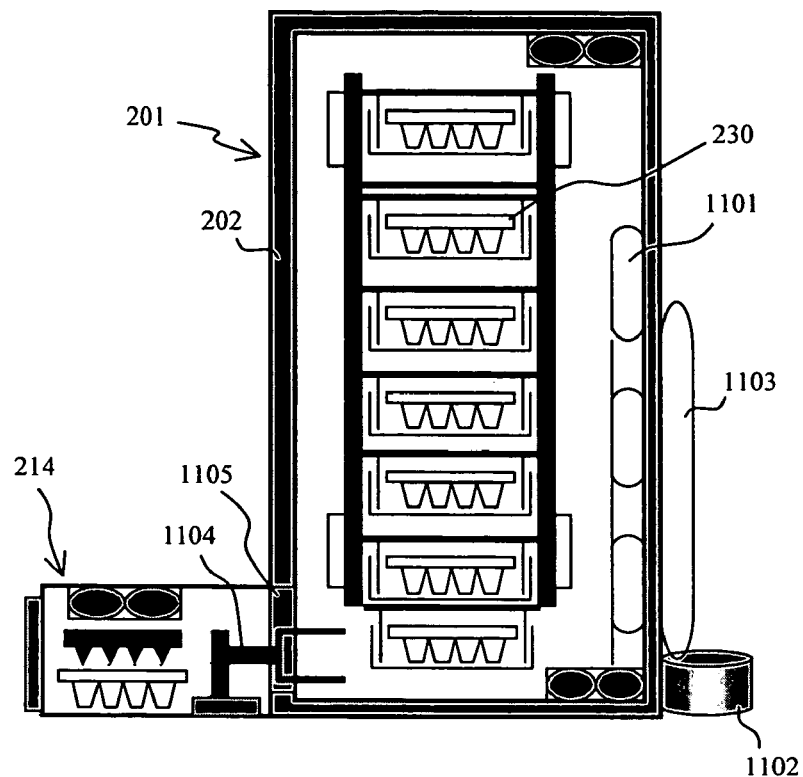
FIGS. 11A and 11B schematically show a sample plate storage unit in a second example of the electrophoresis apparatus.
Figure 11:
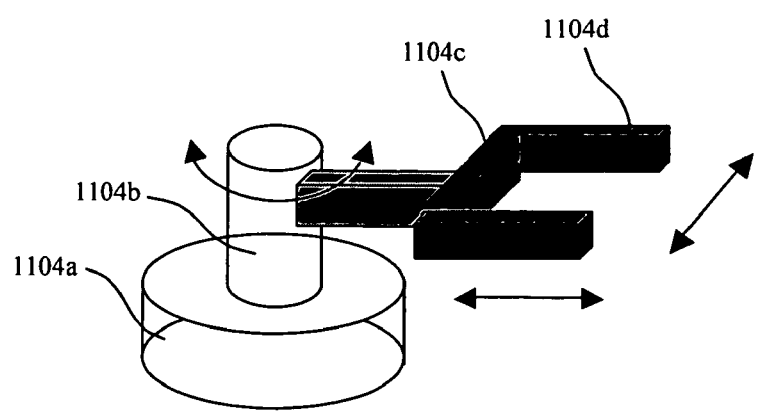

With reference to FIG. 11, a second embodiment of the invention is described, particularly with regard to the difference from the first embodiment shown in FIG. 2. In this embodiment, the cooling source for the cooling bath 201 of the sample plate storage unit employs a heat pump.

The cooling bath 201 includes a casing 202 constructed of heat-insulating material; a cooler 1101 disposed within the casing 202; a compressor 1102 disposed outside the casing 202; and a radiator 1103, also disposed outside the casing 202. The cooler 1101, compressor 1102, and radiator 1103 are connected, creating a heat-pump type cooling mechanism.

When formaldehyde is used as the diluting solution for the DNA sample, the temperature inside the cooling bath 201 is preferably maintained at minus 15° C. to minus 25° C. Using the heat-pump type cooling mechanism of the present embodiment, the sample plates 230 stored inside the cooling bath 201 can be maintained at minus several tens of degrees Celsius.

Between the cooling bath 201 and the standby unit 214, an entrance 1105 is installed. A loading robot 1104 is provided at the entrance 1105. The loading robot 1104 is used to transport the sample plates 230 stored in the cooling bath 201 to the standby unit.

As shown in FIG. 11B, the loading robot 1104 includes a fixed base 1104a, a rotating axle 1104b rotatably mounted on the fixed base, and an arm 1104c mounted on the rotating axle. The arm 1104c has extendible claws 1104d, via which the arm can hold a sample plate 230 in a horizontal position, when the rotating axle 1104b can be rotated by 180 degrees. In this way, the sample plate 230 held by the claws can be transported from the cooling bath 201 to the standby unit 214.

In the sample storage unit of the present embodiment, the heating mechanism 216 (shown in FIG. 2) is omitted. The sample plates 230 are left to stand at room temperature for 10 minutes, for example, in the standby unit 214. In this way, the samples in the wells of the sample plates 230 can be thawed and readied for analysis.

Embodiment 3

Figure 12:
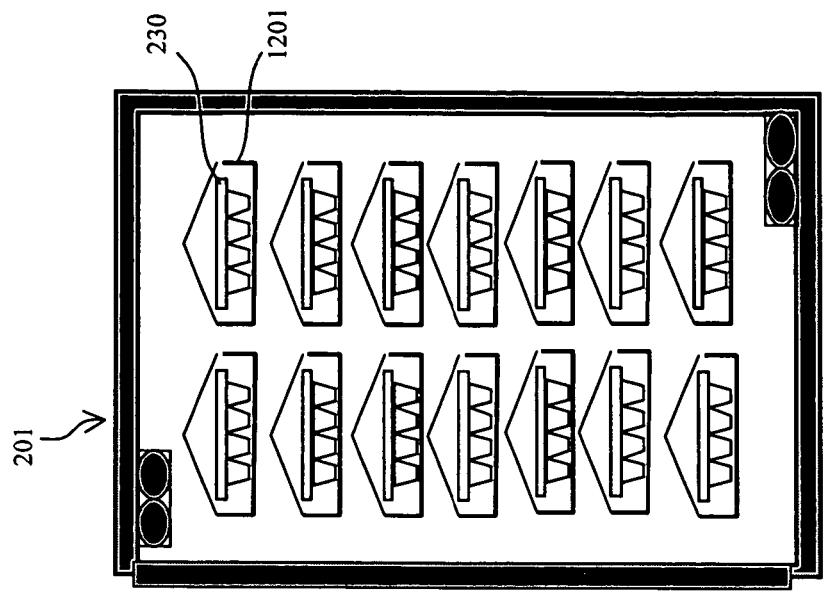
FIGS. 12A and 12B schematically show a sample plate storage unit in a third example of the electrophoresis apparatus.
Figure 12:
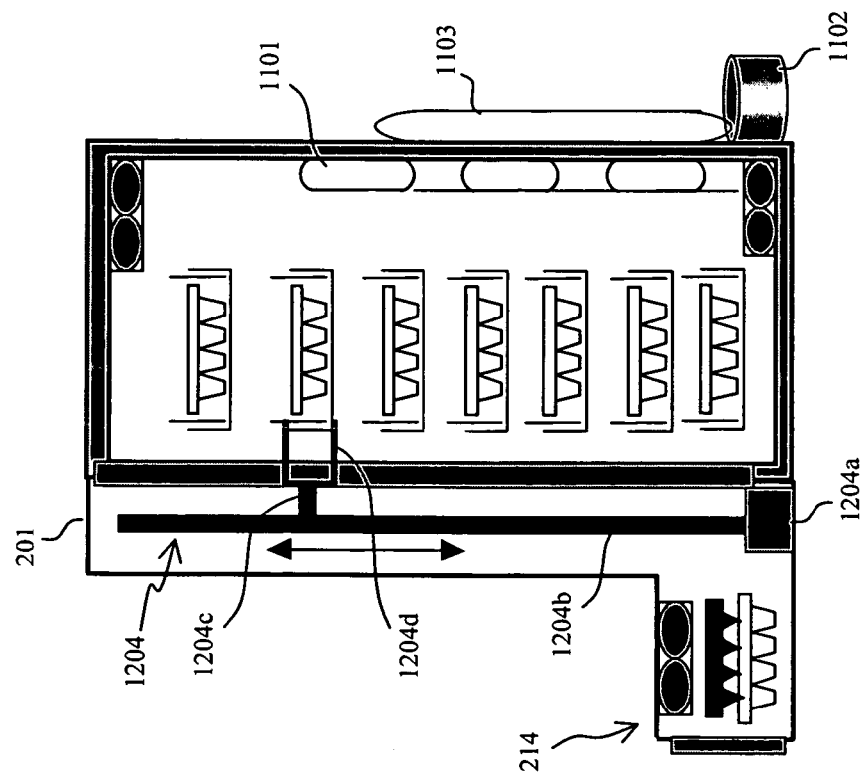

With reference to FIG. 12, a third embodiment of the electrophoresis apparatus of the invention is described, particularly with regard to the difference from the second embodiment shown in FIG. 11. In the present embodiment, the racks in the cooling bath 201 are mounted in a fixed manner, rather than in the Ferris wheel fashion. For the transport of the sample plates 230, a loading robot is installed.

Inside the cooling bath 201, a loading robot 1204 is provided for transporting racks 1201 disposed in the vertical direction at regular intervals, and the sample plates on the racks. The racks 1201 are disposed in two rows, for example.

The loading robot 1204 includes a movable base 1204a which is horizontally movable, a rotating axle 1204b rotatably mounted on the movable base, and an arm 1204c movably mounted on the rotating axle. The arm 1204c includes extendable claws 1204d.

Initially, the movable base 1204a is moved horizontally and placed in front of the row of racks on which sample plates as the analyzed objects are stored. The arm 1204c disposed at the lower end is then moved vertically upward and stopped at the height of a particular rack on which a sample plate of interest is placed. The sample plate 230 is held by the claws 1204d in a horizontal position, and the rotating axle 1204b is rotated by 180°. Then, the arm 1204c is moved vertically downward and stopped at the lower end. The movable base 1204a is then moved horizontally and stopped in front of the standby unit 212. The sample plate 230 held by the claws 1104d is thus transported to the standby unit 214.

When transporting a sample plate that has been analyzed from the standby unit 214 to the rack within the cooling bath 201, the opposite operation is carried out.

While specific examples of the invention have been described above, it is to be understood that various modifications and variations may be without departing from the scope of the following claims.

What is claimed is:

1. An electrophoresis apparatus comprising:
   an electrophoresis analysis unit that analyzes a sample disposed on a sample plate by electrophoresis;
   a freezing storage bath capable of freezing a plurality of sample plates and accommodating said frozen sample plates;
   a standby unit that temporarily stores one of said sample plates before said sample plate is transported to said electrophoresis analysis unit; and
   a transport unit that transports said sample plate,
   wherein a frozen sample plate which was transported from said freezing storage bath to said standby unit is thawed and is stored in said standby unit while another sample plate is being analyzed in said electrophoresis analysis unit.

2. The electrophoresis apparatus according to claim 1, wherein said standby unit heats said sample plate.

3. The electrophoresis apparatus according to claim 1, wherein said standby unit removes condensation on said sample plate by air circulation.

4. The electrophoresis apparatus according to claim 1, wherein said standby unit removes a film on said sample plate.

5. The electrophoresis apparatus according to claim 1, further comprising a sample detector that reads an identification code affixed to said sample plate.

6. The electrophoresis apparatus according to claim 1, further comprising a display unit that visually displays information about and the state of said sample plates stored in said freezing storage bath and said standby unit.

7. An electrophoresis apparatus comprising:
- an electrophoresis analysis unit that analyzes a sample disposed on a sample plate by electrophoresis;
- a freezing storage bath that freezes and stores a plurality of sample plates;
- a standby unit that temporarily stores one of said sample plates from said freezing storage bath before said sample plate is transported to said electrophoresis analysis unit;
- a transport unit that transports one of said sample plates stored in said freezing storage bath to said standby unit;
- an entrance provided at the side of said standby unit to be used when an operator carries said sample plate into said standby unit or out from said standby unit;
- a first sample detector that reads an identification code affixed to each of the sample plates stored in said freezing storage bath;
- a second sample detector that reads an identification code affixed to the sample plate stored in said standby unit; and
- a control unit that determines the order of analysis of said sample plates based on the information of said sample plates.

8. The electrophoresis apparatus according to claim 7, further comprising a display unit that visually displays the order of analysis of said sample plates.

9. The electrophoresis apparatus according to claim 7, wherein said control unit determines the order of analysis based on sample conditions.

10. The electrophoresis apparatus according to claim 7, wherein said control unit determines the order of analysis such that sample plates with identical sample conditions are analyzed successively.

11. The electrophoresis apparatus according to claim 7, wherein said control unit determines the order of analysis based on the storage time, capillary length, and/or electrophoresis temperature of said sample.

12. The electrophoresis apparatus according to claim 7, wherein, when a sample plate that requires emergency analysis exists among said sample plates stored in said freezing storage bath, said control unit determines the order of analysis again such that said sample plate for emergency analysis is given preference.

13. The electrophoresis apparatus according to claim 7, wherein said control unit determines a sample plate for which analysis must be repeated, based on the result of analysis obtained by said electrophoresis analysis unit.

14. The electrophoresis apparatus according to claim 7, wherein, based on the result of analysis obtained by said electrophoresis analysis unit, said control unit terminates the analysis of a sample plate that has the same sample conditions as those of a sample plate of which the analysis result has been defective.

* * * * *